(12) United States Patent
Shi et al.

(10) Patent No.: US 11,273,165 B2
(45) Date of Patent: Mar. 15, 2022

(54) APPLICATIONS FOR ESTRADIOL IN PREPARING ANTI-SMALL CELL LUNG CANCER AND/OR OVARIAN CANCER AND/OR OSTEOSARCOMA PRODUCTS

(71) Applicant: SHANGHAI JIAO TONG UNIVERSITY, Shanghai (CN)

(72) Inventors: Yongyong Shi, Shanghai (CN); Zhijian Song, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 16/453,397

(22) Filed: Jun. 26, 2019

(65) Prior Publication Data
US 2020/0085841 A1 Mar. 19, 2020

Related U.S. Application Data

(63) Continuation of application No. 15/740,766, filed as application No. PCT/CN2015/000474 on Jun. 30, 2015, now abandoned.

(51) Int. Cl.
*A61K 31/565* (2006.01)
*A61P 35/00* (2006.01)

(52) U.S. Cl.
CPC ............ *A61K 31/565* (2013.01); *A61P 35/00* (2018.01)

(58) Field of Classification Search
CPC .... A61K 31/565; A61K 2300/00; A61P 35/00
See application file for complete search history.

(56) References Cited

U.S. PATENT DOCUMENTS

2018/0185386 A1    7/2018  Shi et al.

FOREIGN PATENT DOCUMENTS

CN          1660437 A       8/2005
WO    WO-2010/133604 A1    12/2010

OTHER PUBLICATIONS

Zhu et al., "Oestrogen receptor alpha mediates 17beta-estradiol enhancement of ovarian cancer cell motility through up-regulation of survivin expression," Arch. Gynecol. Obstet. Sep. 2012;286(3):729-37. PMID: 22569715. (Year: 2012).*
Laviolette et al., "17beta-estradiol accelerates tumor onset and decreases survival in a transgenic mouse model of ovarian cancer," Endocrinology. Mar. 2010;151(3):929-38. PMID: 20056833. (Year: 2010).*
Langdon et al., "Contrasting effects of 17 beta-estradiol on the growth of human ovarian carcinoma cells in vitro and in vivo," Int. J. Cancer Sep. 30, 1993;55(3):459-64. PMID: 8375930. (Year: 1993).*
SKOV-3 Detailed product information retrieved from American Tissue Culture Collection (atcc.org/products/htb-77) on Nov. 24, 2021. (Year: 2021).*
Alexandrov K, Cascorbi I, Rojas M, Bouvier G, Kriek E, Bartsch H. CYP1A1 and GSTM1 genotypes affect benzo[a]pyrene DNA adducts in smokers' lung: comparison with aromatic/hydrophobic adduct formation. Carcinogenesis. Dec. 2002; 23(12): 1969-77. Review. PubMed PMID: 12507920. (Year: 2002).
Chen et al., "Protection effects and mechanism of 17β-estradiol in high homocysteine induced injury of human osteosarcoma MG63 cells in vitro", Acta Anatomica Sinica, vol. 42, No. 5, Oct. 2011, pp. 635-639.
English-Language Translation of Li et al., prepared by USPTO contractor, Dec. 2018. (Year: 2018).
Hsu LH, Chu NM, Kao SH. Estrogen, Estrogen Receptor and Lung Cancer. Int J Mol Sci. Aug. 5, 2017; 18(8). pii: E1713. PubMed PMID: 28783064; PubMed Central PMCID: PMC5578103. (Year: 2017).
International Search Report and Written Opinion for Appl. Ser. No. PCT/CN2015/000474 dated Jan. 5, 2017 (10 pages).
International Search Report and Written Opinion for Appl. Ser. No. PCT/CN2015/000474 dated Mar. 21, 2016 (10 pages).
Li et al., "Inhibition of estradiol on tumorigenesis of benzo(a)pyrene induced lung tumors in male Kunming mice", Chin J Public Health, vol. 24., No. 5, May 2008, pp. 548-549.
Li et ai., "Inhibitory Effects of Estradiol on Benzo(a)pyrene-Induced Lung Cancer in Male Mice," Chinese Journal of Public Health, May 2008, vol. 24, No. 5, pp. 549-49. (Year: 2008).
Lin P, Chang H, Tsai WT, Wu MH, Liao YS, Chen JT, Su JM. Overexpression of aryl hydrocarbon receptor in human lung carcinomas. Toxicol Pathol. Jan.-Feb. 2003; 31(1): 22-30. PubMed PMID: 12597446. (Year: 2003).
Nakanishi Y, Cuttitta F, Kasprzyk PG, Avis I, Steinberg SM, Gazdar AF, Mulshine JL. Growth factor effects on small cell lung cancer cells using a colorimetric assay: can a transferrin-like factor mediate autocrine growth? Exp Cell Biol. 1988; 56(1-2): 74-85. PubMed PMID: 2846378. (Year: 1988).
Non-Final Office Action on U.S. Appl. No. 15/740,766 dated Dec. 27, 2018.
Ohsaki Y, Yang HK, Le PT, Jensen RT, Johnson BE. Human small cell lung cancer cell lines express functional atrial natriuretic peptide receptors. Cancer Res. Jul. 1, 1993; 53(13): 3165-71. PubMed PMID: 8391389. (Year: 1993).
Zhu, Jing, "Effects of estrogen receptor a and β on the proliferation and invasion of ovarian carcinomas", Medicine & Public Health, China Doctoral Dissertations Full-Text Database (Electronic Journals), Feb. 2007, pages E072-E137.

(Continued)

*Primary Examiner* — Theodore R. Howell
(74) *Attorney, Agent, or Firm* — Foley & Lardner LLP

(57) ABSTRACT

This invention discloses uses for estradiol in preparing anti-small cell lung cancer and/or ovarian cancer and/or osteosarcoma products. This invention provides uses for estradiol in preparing anti-small cell lung cancer and/or ovarian cancer and/or osteosarcoma products. From carrying out cancer drug repositioning for the FDA- and CFDA-approved drug estradiol, experiments for this invention show, based on screening of non-anti-cancer drugs for various cancer cell lines (tissue types) and mutation sites, that estradiol has a new use as an anti-small cell lung cancer and/or ovarian cancer and/or osteosarcoma medication, thus achieving a new purpose for an old drug.

4 Claims, 2 Drawing Sheets

(56) References Cited

OTHER PUBLICATIONS

Aapro, et al., "Doxorubicin versus doxorubicin and cisplatin in endometrial carcinoma: definitive results of a randomized study (55872) by the EORTC Gynaecological Cancer Group", Annals of Oncology 14: 441-448, 2003.

\* cited by examiner

|   | 1 | 2 | 3 | 4 | 5 | 6 | 7 | 8 | 9 | 10 | 11 | 12 |
|---|---|---|---|---|---|---|---|---|---|---|---|---|
| A | DMSO | S1208(→) | | | | | | | | | DMSO | S1208 |
| B | | Cpd1(→) | | | | | | | | | | |
| C | | | | | | | | | | | | |
| D | | Cpd2(→) | | | | | | | | | | |
| E | S1208 | | | | | | | | | | | DMSO |
| F | | Cpd3(→) | | | | | | | | | | |
| G | | | | | | | | | | | | |
| H | | S1208(→) | | | | | | | | | | |
Figure 1
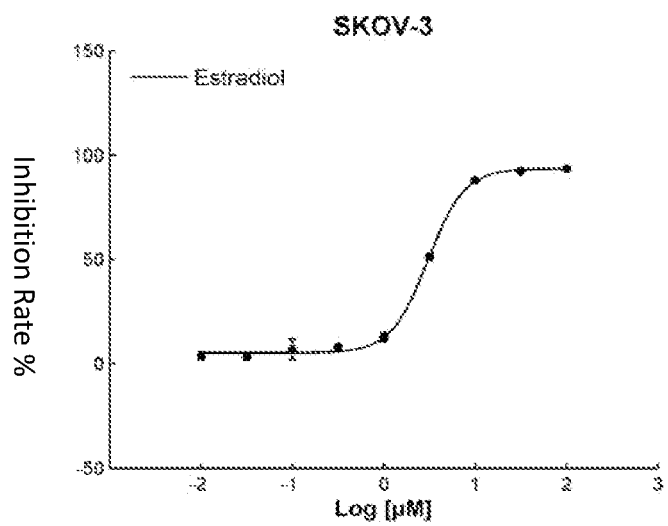
Figure 2
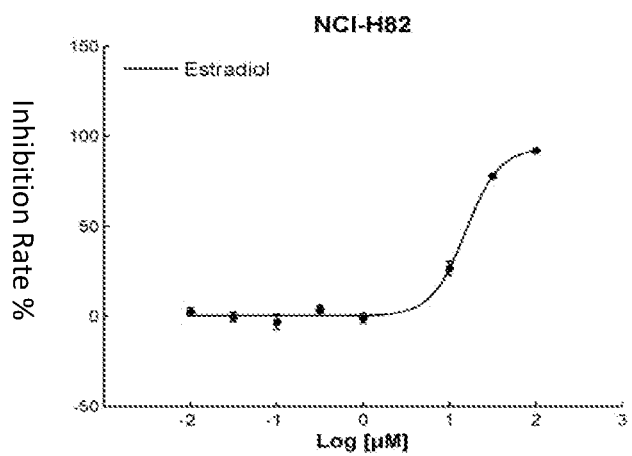
Figure 3

APPLICATIONS FOR ESTRADIOL IN PREPARING ANTI-SMALL CELL LUNG CANCER AND/OR OVARIAN CANCER AND/OR OSTEOSARCOMA PRODUCTS

CROSS-REFERENCE TO RELATED APPLICATIONS

This application is a continuation of U.S. patent application Ser. No. 15/740,766, filed Dec. 28, 2017, which is a National Stage Application of PCT/CN2015/000474, filed Jun. 30, 2015, the entire contents of both of which are incorporated herein by reference.

TECHNICAL FIELD

The present invention relates to the technical field of biology, and it particularly relates to the application of estradiol in the preparation of anti-small cell lung cancer and/or ovarian cancer and/or osteosarcoma products.

BACKGROUND

Cancer is the most common as well as the most serious disease that threatens human health, and developing effective anti-cancer medications is critical to extending patients' lives. Along with the rapid development of cancer genomics and molecular pharmacology in recent years, the development of new anti-cancer medications has had relatively good outcomes. However, since the bottlenecks of large investments required in the development of new medications and the long-time periods cannot be overcome, as well as the great individual variation in tumor genetics, many traditional anti-cancer medications are not very effective, new medications are expensive, and side effects are not well understood.

In a paper published by the researchers Barabasi A L et. al. in the 2011 Nature Reviews Genetics, a molecular network analysis conducted based on GWAS findings and an interactome strategy is expected to reveal new drug targets and molecular markers for complex diseases, and ultimately to provide an entirely new understanding of disease pathogenesis and treatment approaches. Even more noteworthy is that it has been discovered in drug repositioning studies that susceptibility genes locked in by GWAS studies as well as their genes with protein-protein interaction (PPI) can more easily become indirect targets for medications. This discovery aids in explaining the mechanisms of action of currently available drugs as well as guiding new drug research. In 2014, researchers Okada Y et. al. published a paper in Nature showing that out of the 101 susceptibility genes for rheumatoid arthritis found through a meta-analysis of GWAS findings, 98 are currently being used as direct or indirect targets for rheumatoid arthritis medications. They also discovered through drug repositioning research that there are dozens of medications that have been approved for use for other indications that could be used to treat rheumatoid arthritis.

DISCLOSURE

This research was carried out through integrating cancer gene profiles of the Cancer Gene Census of the Cosmic version 72 cancer histological database as well as the protein interactions in the STRING version 10 database with Drug Bank Version 4.2, the database of FDA approved medications. This obtained candidates for drug repositioning and screening tests for tumor cell lines were carried out, revealing new anti-cancer drugs. Candidates for tumor suppressing drugs revealed from the cancer cell line screening are as follows:

nicardipine, promethazine, estrone, estradiol, sulindac, etonogestrel, levonorgestrel, mesalazine, indomethacin, sulfasalazine, balsalazide, irbesartan, ibuprofen, isoprenaline, and pentosan polysulfate.

The primary goal of this invention is to provide a new use for estradiol.

This invention provides uses for estradiol in preparing anti-small cell lung cancer and/or ovarian cancer and/or osteosarcoma products.

The second goal of this invention is to provide a new use for estradiol.

This invention provides uses for estradiol in the preparation of products to inhibit the proliferation of anti-small cell lung cancer and/or ovarian cancer and/or osteosarcoma.

The third goal of this invention is to provide a new use for estradiol.

This invention provides uses for estradiol in the preparation of products to reduce the IC50 values of anti-small cell lung cancer and/or ovarian cancer and/or osteosarcoma cells.

Use of estradiol in treating anti-small cell lung cancer and/or ovarian cancer and/or osteosarcoma are also within scope of protection of this invention.

Use of estradiol in inhibiting the proliferation of anti-small cell lung cancer and/or ovarian cancer and/or osteosarcoma are also within scope of protection of this invention.

Use of estradiol as a medication for treating anti-small cell lung cancer and/or ovarian cancer and/or osteosarcoma are also within scope of protection of this invention.

Use of estradiol as a medication for inhibiting the proliferation of anti-small cell lung cancer and/or ovarian cancer and/or osteosarcoma are also within scope of protection of this invention.

In the application above, the small-cell lung cancer cells mentioned are NCI-H82, the ovarian cancer cells mentioned are SKOV-3, and the osteosarcoma cells mentioned are U2OS.

In the uses above, the product is a medication or reagent kit.

The fourth goal of this invention is to provide a kind of product.

The active ingredient in the product provided by this invention is estradiol, and this product has at least one of the following functions:

1) Treatment of small-cell lung cancer and/or ovarian cancer and/or osteosarcoma;
2) Inhibition of the proliferation of small cell lung cancer cells and/or ovarian cancer cells and/or osteosarcoma cells;
3) Reduction of the IC50 values of small cell lung cancer cells and/or ovarian cancer cells and/or osteosarcoma cells;

In the products described above, the small-cell lung cancer cells mentioned are NCI-H82, the ovarian cancer cells mentioned are SKOV-3, and the osteosarcoma cells mentioned are U2OS.

In the product above, the product is a medication or reagent kit.

BRIEF DESCRIPTION OF THE DRAWINGS

FIG. 1 is a distributed 96-well drug screening culture plate.

FIG. 2 is estradiol sensitivity to ovarian cancer; EC50=3.0280; IC50=3.0662; $R^2$=0.9990.

FIG. 3 is estradiol sensitivity to small-cell lung cancer; EC50=15.2786; IC50=16.2549; $R^2$=0.9971.

BEST MODE TO CARRY OUT THE INVENTION

Figure 4:
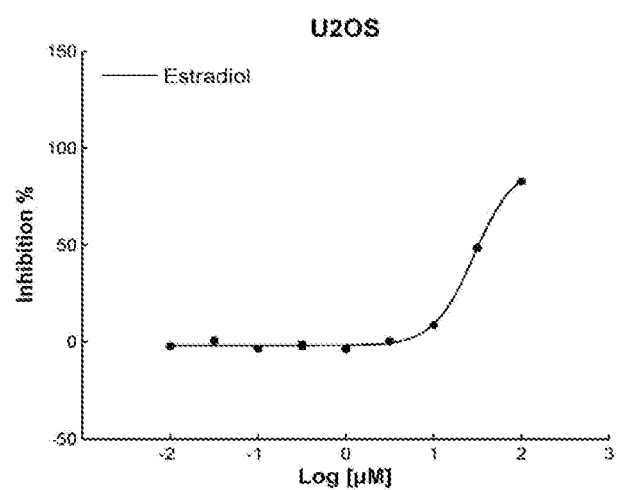
FIG. 4 is estradiol sensitivity to osteosarcoma; EC50=28.7837; IC50=32.6945; $R^2$=0.9983.

Unless otherwise specified, the experimental methods employed in the following examples are standard methods.

Materials, reagents, etc. used in the following examples are all commercially available unless otherwise specified, and the experimental methods employed in the following examples are standard methods.

The analyte drug in the following examples is estradiol, and its chemical composition is:

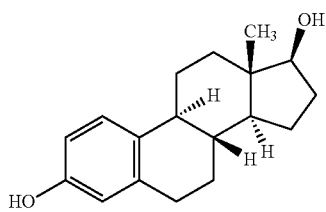

It is a drug bank product with a catalog number of DB00783.

In the examples below, the product sources for the NCI-H82 small-cell lung cancer cells, the SKOV-3 ovarian cancer cells, the SNU-475 and NCI-H810 human hepatoma cells, and the U2OS osteosarcoma cells are as follows:

| | | |
|---|---|---|
| NCI-H810 | ATCC | CRL-5816 |
| NCI-H82 | ATCC | HTB-175 |
| SKOV-3 | ATCC | HTB-77 |
| SNU-475 | ATCC | CRL-2236 |
| U2OS | ECACC | 92022711 |

The primary instruments and materials in the examples below are:

DMSO (from Sigma, Cat. No. D4540)

96-well clear bottom cell culture plates (from Corning, Cat. No. 3610)

CellTiter Glo reagent kit (from Promega, Cat. No. G7573)

Doxorubicin positive medication (from MCE, Cat. No. HY-15142)

Fetal Bovine Serum (from Gibco, Cat #10099141)
100 mm petri dish (from Corning, Cat #430167)
RPMI-1640 medium (from Gibco, Cat #A1049101)
DMEM medium (from Gibco, Cat #11995081)
DMEM/F12 medium (from Gibco, Cat #11330057)
EMEM medium (from Gibco, Cat #10370021)
Multidrop 384 cell dispensers (Thermo, Cat #5840150)
EnSpire multi-function plate reader (Perkin Elmer, Cat #2300-001M)

In example 1, CELLTITER-GLO was used to test estradiol against small-cell lung cancer and/or ovarian cancer and/or osteosarcoma epithelial cell carcinoma A. Test Plate Preparation 1. Cell plating a) The complete medium required for each cell was prepared.

b) Before beginning the experiment, the name of the drug screened for the cells marked on the 100 mm petri dish was confirmed as well as information such as the passage time and number of passages to ensure the experiment was error-free.

c) Refer to steps d) through i) for procedures for adherent cells; refer to steps j) through l) for procedures for suspension cells.

d) When using aseptic technique, a vacuum pump was used to draw the cell culture medium.

e) 2 ml of a sterile PBS solution was used to rinse the cell surface, and a vacuum pump was used to aspirate the PBS waste.

f) A 1 ml 0.25% (w/v) Trypsin-0.038% (w/v) EDTA solution was gently added to the petri dish for cell digestion, and after gently mixing several times, the solution covered the cell surfaces. The status of cell digestion was observed under an inverted microscope, and the trypsin digestion effect was terminated when cell shedding was about to occur.

g) 5 ml of pre-warmed 37° C. complete medium was added to the petri dishes, and a pipette was used to gently dissociate the cells in order for them to shed from the bottom of the petri dish.

h) The cells were suspended and transferred to a 15 ml or 50 ml sterile centrifuge tube and they were centrifuged at 1000 rpm for 5 minutes.

i) A vacuum pump was used to aspirate the medium with aseptic technique. 5 ml of pre-warmed 37° C. complete medium was used to resuspend the cell sediment, and it was gently dissociated to mix evenly.

j) A pipette was used to gently dissociate the cells so that they fully shed from the bottom of the petri dish.

k) The cells were suspended and transferred to a 15 ml or 50 ml sterile centrifuge tube and they were centrifuged at 1000 rpm for 5 minutes.

l) A vacuum pump was used to aspirate the medium with aseptic technique. 5 ml of pre-warmed 37° C. complete medium was used to resuspend the cell sediment, and it was gently dissociated to mix evenly.

m) A cell counter was used to count the number of suspended cells and adjust the cell suspension to an appropriate density in the plate to carry out cell plating experiments.

NCI-H82 cells and SKOV-3 cells were handled as described above, and NCI-H82 96-well cell culture plates and SKOV-3 96-well cell culture plates were obtained, respectively.

The complete medium for NCI-H82 cells was RPMI-1640 (a live product), Cat #A1049101, with a cells/well density of 12000.

The complete medium for SKOV-3 cells was McCOY'S 5A (a live product), Cat #16600082, with a cells/well density of 12000.

2. The drug analyte estradiol was prepared and administered (200× final concentration):

1) The master plate for the drug analyte estradiol was prepared a) DMSO was used to dilute the analyte estradiol to 20 mM for use.

b) 79 µL of the 20 mM analyte prepared in step a) was added to the first well in the first row of the dilution plate, and then 54 µL of DMSO solution was added to the second through ninth wells of the first row. 25 µL of solution was aspirated from the first to the second well, and after mixing well 25 µL of solution was aspirated from the second to the third well, and this was repeated until the 9th well in order to ensure that 3.16 dilution of the medication would be carried out one-by-one.

2) Doxorubicin positive medication (MCE, Cat. No. HY-15142) master plate preparation
  a) DMSO was used to dilute Doxorubicin positive medication to 6 mM for use.
  b) The 6 mM Doxorubicin positive medication solution was added to the dilution plate, and the DMSO solution was incrementally added to the analyte medication to 1:3.16.

3. Drug working board preparation and dosing
  a) The analyte drug and the positive drug sampling template is as shown in FIG. 1, in which S1208: Positive medication Doxorubicin, DMSO: Positive control well, Cpd 1, 2, 3: Analyte drug, with a DMSO final concentration of 0.5% (DMSO compatibility).
  b) 95 µl of cell-specific complete medium was added to the working plate, each medication to 9 wells. A multi-channel pipettor was used to transfer a series of 5 µl (9 wells) of the diluted solution of the analyte drug and positive medication Doxorubicin (10× final concentration) from the working plate, achieving cell culture media of varying concentrations.
  c) The NCI-H82 96 well cell plates and the SKOV-3 96-well cell plates prepared in step 1 were removed from the incubator, and 10 µl of the cell culture media (10× final concentration) with varying drug concentrations as described in b) above was added to the NCI-H82 well cell culture and the SKOV-3 96-well cell culture plate row-by-row as shown in FIG. 1. It was placed into a $CO_2$ incubator at 37° C. for 72 hours, obtaining the NCI-H82 96-well drug screening plate and the SKOV-3 96-well drug screening plate.

Wells with no medication added acted as controls.

The final concentrations and dosing of the analyte drug, positive medication Doxorubicin, and control in the 96-well plates were as follows:

The final concentrations (µM) of the analyte drug in wells 2-10 in FIG. 1 are, in order: 100, 31.64557, 10.01442, 3.16912, 1.002886, 0.317369, 0.100433, 0.031783, 0.010058;

The final concentration (µM) of the positive medication Doxorubicin in wells 2-10 in FIG. 1 are, in order: 30, 9.493671, 3.004326, 0.950736, 0.300866, 0.095211, 0.03013, 0.009535, 0.003017;

In addition, the S1208 well in the 96-well plate (E1-H1 and A12-D12): 10 µl of the final concentration 100 µM Doxorubicin solution (solvent containing 0.5% DMSO complete culture medium solution), DMSO wells (A1-D1, E12-H12, and A11-H11): 10 µl containing 0.5% DMSO complete culture medium solution.

B. CELLTITER-GLO Luminescent Cell Viability Assay System
  1. CellTiter-Glo reagent preparation
    a) The CellTiter-Glo reagent buffer was thawed before using and stabilized to room temperature for use.
    b) The CellTiter-Glo reagent frozen substrate was thawed before using and stabilized to room temperature for use.
    c) 100 ml of stabilized CellTiter-Glo buffer was added to the container with CellTiter-Glo reagent frozen substrate to adequately resuspend it to form an enzyme/substrate mixture, also referred to as the CellTiter-Glo assay reagent.
    d) It was gently mixed and vortexed and inverted multiple times to achieve a uniform solution. In general, the CellTiter-Glo substrate reagent will adequately dissolve within 1 minute. It is stored separately in low-light conditions at −20° C. to await use, and freezing repeatedly should be avoided.

2. Testing
    a) Before testing, the NCI-H82 96-well drug screening plate and the SKOV-3 96-well drug screen plate described in 3 above were stabilized to room temperature for 20-30 minutes.
    b) An inverted microscope was used to observe the conditions of each group of cells in the culture plate and their death patterns, and any abnormal conditions were noted and retested.
    c) 100 µl of CellTiter-Glo reagent (prepared as described in 1 above) was added to all drug screening plates and mixed evenly.
    d) It was thoroughly oscillated in a 96-well microplate oscillator for 2 minutes to allow the cells to undergo full lysis.
    e) It was stored away from light at room temperature for 15 minutes before carrying out luminescent signal detection to ensure signal stability.
    f) An EnSpire multi-function plate reader was used at 570 nm to read the luminescent signals.
    g) Data was processed and analyzed.

The results of the NCI-H82 96-well drug screening plate are shown in FIG. 2.

The results of the SKOV-3 96-well drug screening plate are shown in FIG. 3.

The IC50 value was calculated; results are shown in Table 1.

The same method was used to test estradiol's action on the IC50 value of U2OS osteosarcoma cells. Results are in Table 1 and FIG. 4. The complete medium for U2OS cells was DMEM (a live product), Cat #11995081 with a cells/well density of 3000.

The same method was used to test estradiol's action on the IC50 value of SNU-475 human hepatoma cells and NCI-H810 human hepatoma cells; results are shown in Table 1.

It is evident that estradiol has a specific inhibitory effect on the proliferation of small lung cancer cells and/or ovarian cancer cells and/or osteosarcoma cells and it can be used as a medication for small lung cancer and/or ovarian cancer and/or osteosarcoma treatment.

TABLE 1

| IC50 values of various cells under the effect of estradiol | |
|---|---|
| Cells | IC50 value |
| SKOV-3 | 3.0662 |
| SNU-475 | 100 |
| NCI-H82 | 16.2549 |
| NCI-H810 | 100 |
| U2OS | 32.6945 |

INDUSTRIAL APPLICATIONS

From carrying out cancer drug repositioning for the FDA- and CFDA-approved drug estradiol, experiments for this invention show, based on screening of non-anti-cancer drugs for various cancer cell lines (tissue types) and mutation sites, that estradiol has a new use as an anti-small cell lung cancer and/or ovarian cancer and/or osteosarcoma medication, thus achieving a new purpose for an old drug.

What is claimed is:

1. A method of inhibiting the proliferation of ovarian cancer cells comprising contacting the cells with an effective amount of estradiol at a concentration of about 0.1 μM or higher.

2. The method of claim 1, wherein the ovarian cancer cells are SKOV-3 cells.

3. The method of claim 1, wherein the cells are resistant to cytotoxic drugs.

4. An in vitro method of inhibiting the proliferation of ovarian cancer cells comprising contacting the cells with an effective amount of estradiol at a concentration of about 0.1 μM or higher.

* * * * *